United States Patent [19]

Wachter et al.

[11] Patent Number: 5,242,940

[45] Date of Patent: Sep. 7, 1993

[54] PHARMACOLOGICALLY ACTIVE N-1 AND C-5 HETEROCYCLIC PYRAZOLES AND METHOD FOR SYNTHESIZING THE SAME

[75] Inventors: Michael P. Wachter, Bloomsburg; William V. Murray, Belle Mead, both of N.J.

[73] Assignee: Ortho Pharmaceutical Corporation, Raritan, N.J.

[21] Appl. No.: 810,346

[22] Filed: Dec. 17, 1991

Related U.S. Application Data

[60] Division of Ser. No. 563,724, Aug. 6, 1990, abandoned, which is a continuation of Ser. No. 303,072, Jan. 30, 1989, abandoned, which is a continuation of Ser. No. 55,808, May 29, 1987, abandoned.

[51] Int. Cl.$^5$ .................. C07D 409/04; A61K 31/415
[52] U.S. Cl. ...................................... 514/406; 514/341; 514/367; 514/252; 514/333; 548/179; 548/180; 548/540; 548/365.7; 548/364.1; 546/279; 546/256; 546/315; 544/238; 549/72
[58] Field of Search ......................... 514/406; 548/374

[56] References Cited

U.S. PATENT DOCUMENTS 4,095,025 6/1978 Newberry ........................ 548/378

Primary Examiner—Jane T. Fan
Attorney, Agent, or Firm—Ralph R. Palo

[57] ABSTRACT

N-1 and C-5 heterocyclic pyrazoles, a method of their preparation, compositions containing the same and methods of their use are disclosed. The pyrazoles are useful in alleviating inflammatory and cardiovascular disorders in mammals.

6 Claims, No Drawings

PHARMACOLOGICALLY ACTIVE N-1 AND C-5 HETEROCYCLIC PYRAZOLES AND METHOD FOR SYNTHESIZING THE SAME

This is a division of application Ser. No. 563,724, filed Aug. 6, 1990, now abandoned which is a continuation of Ser. No. 07/303,072 filed Jan. 30, 1989 abandoned, which is a continuation of Ser. 07/055,808, filed May 29, 1987 abandoned.

TECHNICAL FIELD

The present invention relates to N-1 and C-5 heterocyclic pyrazole derivatives which are pharmacologically active in alleviating inflammation, asthma, hypersensitivity, myocardial ischemia, dermatological conditions such as psoriasis, dermatitis and gastrointestinal inflammatory conditions such as inflammatory bowel syndromes, and to a method for synthesizing those pyrazole derivatives.

BACKGROUND

Nonsteroidal anti-inflammatory drugs (NSAID's) such as indomethacin, naproxen, ibuprofen, tolectin, fenoprofen and the like have generally been shown to attenuate the biosynthesis of prostaglandins by inhibiting the activity of the enzyme cyclooxygenase. The prostaglandin end-products of the cyclooxygenase pathway are responsible for many of the early signs of inflammation including hyperalgesia, increases in vascular permeability leading to edema, and pyrexia. The activity and potency or the NSAID's in reducing these signs and symptoms is, for the most part, correlated with their ability to inhibit prostaglandin biosynthesis.

The other major pathway of arachidonic acid metabolism is the lipoxygenase pathway. Lipoxygenase products of arachidonate metabolism, the leukotrienes, hydroxyeicosatetraenoic acids (HETES) and hydroperoxyeicosatetraenoic acids (HPETES), have been shown or implicated to be involved in disease states including acute and chronic inflammation, arthritis, allergic and other hypersensitivity disorders, dermatological diseases such as psoriasis, acne, atopic dermatitis, contact sensitivity, eczema and others, cardiovascular disorders secondary to myocardial ischemia or infarction, thromboembolism or vasculitis or platelet aggregation, and hyperalgesic disorders, gynecological disorders such as dysmenorrhea, ocular inflammation, sperm motility or function, and others.

Leukotriene $B_4$ ($LTB_4$), another product of the lipoxygenase pathway, as well as HETES and HPETES can mediate induction of other phlogistic substances such as thromboxanes and prostacyclin, is chemotactic to inflammatory cells, and is hyperalgesic. Many of these mediators have been identified in skin, lungs, coronary circulation, eyes, gastrointestinal tract and other organs, and in the synovial fluid of rheumatoid arthritic patients. In chronic inflammatory conditions such as rheumatoid arthritis, it is believed to be the chronic influx of leukocytes, probably mediated by $LTB_4$, that is the eventual cause of joint erosion.

It is believed that inhibitors of the lipoxygenase pathway could lead to a relatively permanent effect on inflammatory disorders such as rheumatoid arthritis since they could modulate the actual mechanisms of tissue and joint breakdown. Similarly, drugs that could inhibit prostaglandin synthesis via the cyclooxygenase pathway could modulate and reduce early manifestations of inflammation. Pharmacologically active compounds that can inhibit both enzyme pathways at similar concentrations (dual inhibitors) provide a more complete relief for patients suffering from arthritis, hypersensitivity, dermatological, cardiovascular, gastrointestinal, ocular, and gynecological disorders than present drugs that inhibit one pathway, but not the other as is the case for usually used NSAID's that are predominantly inhibitors of the cyclooxygenase (prostaglandin synthesis) pathway.

A number of 1,5-diaryl-3-substituted pyrazoles are reported in the literature. Some of those pyrazoles have been reported to have pharmacological activity.

For example Fulmer et al., *J. Het. Chem.*, 17:799–800 (1980) report the synthesis of 1,3,5-triaryl pyrazoles, as do Foote et al., *J. Het. Chem.*, 7:89–92 (1970), Beam et al., *J. Het. Chem.*, 9:183–185 (1972); Soliman et al., *J. Pharm. Sci.*, 70:606–610 (1981), and Barluenga et al., *J.C.S. Chem. Comm.*, 891 (1979). Soliman et al., *J. Pharm. Sci.*, 70:602–605 (1981) also report synthesis of 3-methyl-1,5-diarylpyrazoles in which the 1-position aryl is a phenylsulfonylurea or thiourea. Of the above reports, only the two reports by Soliman et al. discuss any pharmacological activity for the pyrazoles prepared or for analogs of those pyrazoles, and those materials are reported to have hypoglycemic activity.

Virmani et al., *Indian J. Chem., Sect. B.* 17B: 472–477 (1979) report the synthesis of 3-omega-alkylaminoalkyl pyrazoles among other compounds. The 1,5-diaryl-3-substituted pyrazoles reported contained a phenyl group at the 1-position, a 4-nitrophenyl at the 5-position, and a $(CH_2)_n$—$NHCH_3$ group at the 3-position, where n is 3,4 or 5 (3–5). This report stated that the compounds prepared were screened for a number of biological activities, with nine of the ninety-four numbered compounds synthesized having mild anti-inflammatory activity, two others having diuretic activity and two others having weak anti-cancer activity. The above-discussed 1,5-diaryl-3-substituted pyrazoles were not among the compounds reported to have any pharmacological activity.

Vereshchagin et al., *Zh. Org. Khim.*, 7:907–912 (1971) reported the synthesis of 1,5-diaryl-3-substituted pyrazoles. The 3-substituents were reported to be alkoxy alkylene in which the alkoxy radical was methoxy or phenoxy and the alkylene was methylene or isopropylene, while the 1,5-diaryl radicals were unsubstituted phenyl.

Jahn and Wagner-Jauregg, *Arzneim-Forsch. (Drug Res.)*, 24:494–499 (1974) reported the synthesis and some pharmacological activities of 1,5-diaryl-3-substituted-4,5-dihydropyrazoles. The aryl group at the 1-position for each reported compound was phenyl, while the 5-aryl substituent was reported to be phenyl, 4-methoxyphenyl, 3-methoxy-4-hydroxyphenyl, and 2-hydroxyphenyl. The before-mentioned pyrazoles were substituted at the 3-position by bonding to the 3-position of propionic acid or propiohydroxamic acid. These compounds were said to possess antirheumatic activity.

Shawali et al., *J. Het. Chem.*, 13:989–92 (1976); Shawali, *J. Het. Chem.*, 14:375–81 (1977); and Matsumoto et al., *Bull. Chem. Soc. Japan,* 47: 946–949 (1979) reported the synthesis of 1,5-diaryl-3-subsituted pyrazoles, all of which also included a substituent other than hydrogen at the 4-position on the pyrazole ring. Exemplary 4-position substituents were reported to include cyano, amino, carboethoxy, and phenylcarbonyl.

These reports included no mention of biological activity of the compounds reported.

A series of benzimidoylpyrazoles was reported by Shrof et al., *J. Med. Chem.*, 24:1521-1525 (1981). These compounds were reported to possess activities of sulfonyl urea and biguanide hypoglcemics.

Biere et al., *Arch. Phar.*, 316:608-616 (1983) reported the synthesis of 1,4-diaryl-pyrazole-3-acetic acid derivatives, some of which also contained a an aryl substituent at the 5-position. The synthesized compounds were assayed for use as anti-inflammatory drugs in rats. The compounds assayed that also contained 5-position substituents were reported to be relatively inactive.

A further group of 1,5-diphenyl-4-substituted-pyrazole-3-acetic acids was reported by El-Sayed and Ohta, *Bull. Chem. Soc. Japan*, 46:1801-1803 (1973). Those compounds were utilized as intermediates in the synthesis of pyrazolo-[4,3-c]-pyridines. Another group of 1,5-diphenyl-4-substituted-pyrazoles, some of which also include methyl, phenyl and carboxymethyl groups at the 3-position, was reported in Al-Saleh et al., *J.C.S. Perkin I*, 642-645 (1981) The reports of El-Sayed and Ohta and those of Al-Saleh et al. make no mention of the pharmacological properties of the pyrazole derivatives reported. Another group of 1,5-diaryl-3,4-disubstituted pyrazoles and 4,5-dihydro-5-hydroxy pyrazoles was reported in Fusco and Croce, *Gazz. Chim. Ital.*, 101:703-272 (1971).

SUMMARY OF THE INVENTION

In co-pending application Ser. No. 867,996 filed May 29, 1986, a series of 1,5-substituted pyrazoles is described in which the side chain on the pyrazole ring is unsubstituted.

The present invention contemplates N-1 and C-5 pyrazoles, their use and a method of their synthesis. The compounds of the present invention are pharmacologically active in alleviating inflammation, and inhibit the cyclooxygenase enzyme pathway, the lipoxygenase enzyme pathway, or preferably both pathways.

In particular, the invention contemplates a substituted pyrazole compound having a structure that conforms to the formula

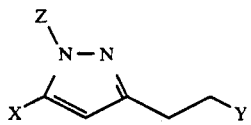

wherein Z is selected from the group consisting of phenyl, substituted phenyl wherein the substitutents are $R_1$ and $R_2$ and $R_1$ and $R_2$ are selected from hydrogen, lower alkyl, lower alkoxy, amino, acetamido, halo, phenyl, hydroxy, lower alkylsulfonyl, lower alkylthio, nitro, trifluoromethyl, ω-trifluoromethyl lower alkoxy, or where $R_1$, $R_2$ are taken together with the phenyl group they form a naphthyl or substituted naphthyl group wherein the substituent is lower alkoxy; a heterocyclic group such as 2-benzothiazolyl, 4-loweralkoxybenzothiazol-2-yl, 2-thiazolyl, 3-substituted pyridazin-6-yl wherein the substituent is halo, substituted pyridin-4-yl, wherein the substituent is halo or dihalo, or thiazolin-2-yl; X is selected from the group consisting of phenyl, substituted phenyl wherein the substituent is $R_3$, $R_4$ and $R_3$, $R_4$ are selected from hydrogen, lower alkyl, lower alkoxy, amido, acetamido, halo, phenyl, hydroxy, lower alkylsulfonyl, lower alkylthio, nitro, trifluoromethyl, ω-trifluoromethyl lower alkoxy, or where $R_3$, $R_4$ are taken together with the phenyl group they form a naphthyl or substituted naphthyl group wherein the substituent is lower alkoxy; 2-thienyl, 3-thienyl, 2-furanyl, 2-N-lower alkoxy pyrollyl and 3-pyridyl; Y is hydroxy lower alkyl, carboxy, CON(OH)lower alkyl or CON(OCOR$_5$)lower alkyl wherein $R_5$ is lower alkyl, provided that at least one of X and Z is a heterocyclic group.

In preferred practice, Z is substituted phenyl, when X is 2-thienyl, 3-thienyl, 2-furanyl, 3-pyridyl or 2-N-lower alkylpyrollyl and Y is carboxy or CONC(OH)lower alkyl; and X is substituted phenyl when Z is 2-benzothiazolyl, substituted 2-benzothiazolyl, 2-thiazolyl or thiazolin-2-yl and Y is hydroxy lower alkyl, carboxy, CON(OH) lower alkyl or CON(OCOCH$_3$) lower alkyl.

The present invention also contemplates a pharmaceutical composition that comprises an anti-inflammatory amount of an above-described substituted pyrazole compound dispersed in a pharmaceutically acceptable carrier. The dose may be administered by topical, p.o., parenteral or aerosol routes. In preferred practice, that substituted pyrazole compound is capable of inhibiting both the cyclooxygenase and the lipoxygenase pathways in the amount present in the composition, when the composition is introduced into a mammal.

Further contemplated is a method for alleviating inflammation in a mammal exhibiting an inflammatory condition. That method comprises administering to that mammal a pharmaceutical composition that includes as the active ingredient an effective amount of an above-described substituted pyrazole compound dispersed in a pharmaceutically acceptable carrier for topical, oral, parenteral and aerosol administration.

Methods for synthesizing a N-1 or C-5 heterocyclic pyrazole are also contemplated.

The present invention provides several benefits and advantages.

A particular benefit of the invention is that it provides pharmacologically active compounds that are useful in treating inflammatory conditions.

Another benefit of the present invention is that some of its pharmacologically active compounds inhibit the cyclooxygenase enzyme pathway, thereby providing a further means for studying that biological process.

Another advantage of the present invention is that some of its pharmacologically active compounds inhibit the lipoxygenase enzyme pathway, thereby providing a further means for studying that biological process.

Still further benefits and advantages of the present invention will be apparent to those skilled in the art from the detailed description and Examples that follow.

DETAILED DESCRIPTION OF THE INVENTION

N-1 and C-5 heterocyclic pyrazole compounds, pharmaceutical compositions containing a substituted pyrazole compound as an active ingredient, a method of treating a mammal exhibiting an inflammatory condition and a method of synthesizing the substituted pyrazole compound are contemplated herein.

In the above formula, $R_1$, $R_2$, $R_3$ and $R_4$ are substituents on phenyl rings that substitute for hydrogen atoms at positions 1 and 5 of the pyrazole ring. It is preferred that at least one of $R_1$ and $R_2$, and one of $R_3$ and $R_4$ be substituted at the 4-positions of their respective phenyl rings.

In examining the above structural formula to which the useful pyrazole compounds conform, it is noted that the $R_1$, $R_2$, $R_3$ and $R_4$ radicals can be a "lower" alkyl, "lower" alkoxy and the like. Groups and radicals referred to as "lower" denote that they possess 1 to about 6 carbon atoms. The same is true for "lower" groups and radicals that are sustituents of the "lower" groups and radicals enumerated.

Lower alkyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, and the like.

Lower alkoxy radicals are oxygen ethers formed from a before-described lower alkyl group. Exemplary radicals include methoxy, ethoxy, propoxy, isopropoxy, n-butoxy, and the like.

Lower alkylthio radicals of $R_1,R_2,R_3$ and $R_4$ are sulfide ethers and are thus analogous to the oxygen ethers described above.

Halo radicals preferably include chloro and bromo, as well as fluoro and iodo.

Lower alkylsulfonyl radicals contain a before-described lower alkyl radical bonded to an $SO_2$ moiety that is itself also bonded to a phenyl ring. Exemplary lower alkylsulfonyl radicals thus include methylsulfonyl, ethylsulfonyl, 2-ethylbutylsulfonyl and the like.

An omega-trifluoromethyl lower alkoxy radical is a lower alkoxy radical as before described that additionally includes a trifluoromethyl group at a position farthest on the alkyl chain from the place of bonding to the phenyl ring. Exemplary of such radicals are the 2,2,2-trifluoroethoxy.

Naphthyl and substituted naphthyl radicals can replace an aryl group herein at either the 1- or 2-positions to provide 1-naphthyl or 2-napththyl substituents, respectfully. Substituents on the naphthyl radicals can be any of those described herein as being useful aryl substituents. Exemplary substituted 1- and 2-naphthyls include 6-methoxy-2-naphthyl and the like.

Lower alkyl carboxy radicals are the before-described lower alkyl radicals that further include a carboxy group. Exemplary lower alkyl carboxy radicals include carboxymethyl, 2-carboxyhexyl and the like. Lower alkyl lower alkoxy carbonyl radicals are lower alkyl esters Of lower alkyl Carboxy radicals. Exemplary lower alkyl lower alkoxy carbonyl radicals include 3-isopropoxycarbonylpropyl, 4-hexyloxycarbonylpentyl and the like.

Pharmaceutically acceptable, non-toxic acid addition salts of the N-1 and C-5 heterocyclic pyrazole compounds are useful herein, and can be formed by treatment of the pyrazole with an appropriate acid. Exemplary inorganic acids include hydrochloric, hydrobromic, sulfuric, phosphoric and the like acids. Exemplary organic acids include methanesulfonic, formic, ethanesulfonic, benzenesulfonic and p-toluenesulfonic and the like acids. Conversely, the acid addition salt form can be converted to the free base form by treatment with alkali.

The substituted pyrazole compounds can include a carboxylic acid and/or a hydroxamic acid, as already noted. Basic salts of those carboxylic and hydroxamic acids are also contemplated, and are formed by treatment of the acid with an appropriate, non-toxic, pharmaceutically acceptable alkaline reagent to form a carboxylate or hydroxamate cation salt. Exemplary non-toxic, pharmaceutically acceptable cation salts of such carboxylic and hydroxamic acids include sodium, potassium, zinc, aluminum, calcium and magnesium. These salts also readily form in aqueous solutions of the carboxylic and hydroxamic acids.

The N-1 and C-5 heterocyclic pyrazoles can be synthesized by treatment of the anion of the appropriately substituted acetyl heterocycle 1 with an appropriate anhydride such as, for example, succinic anhydride to give the heterocyclic diketo acid 2 which is then converted to the corresponding pyrazole alkanoic acid by reaction with an appropriately substituted hydrazine. The pyrazole hydroxamic acid 3 is formed by reacting the acid with an appropriately substituted hydroxylamine. The preparation of the hydroxamic acid is illustrated in Scheme 1 for the case where Z is substituted phenyl and X is pyridyl.

SCHEME 1

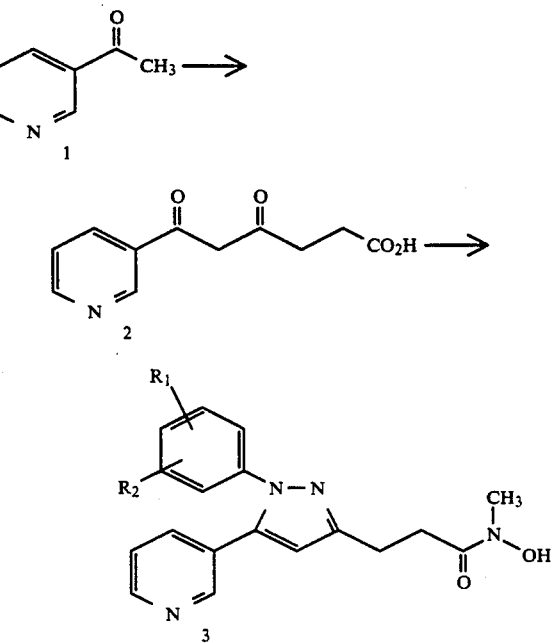

Scheme 2 illustrates the preparation of an N-1 and C-5 substituted pyrazole wherein Z is benzothiazolyl, X is phenyl and Y is CON(OH)lower alkyl. In general, an appropriately substituted hydrazine 4 is reacted with an appropriately substituted 6-aryl-4,6-diketohexanol 5 in an inert solvent such as, for example, methanol, ethanol or isopropanol, with a base such as pyridine, triethylamine or mixtures of the above solvents. The reaction time is typically 1 to about 20 hours depending upon the reactants, the solvent employed and the reaction temperature. The reaction is generally carried out at ambient room temperature although higher temperatures may be employed. In some cases an intermediate 5-hydroxy-2-pyrazoline 6 is obtained which is either isolated and directly oxidized with an oxidizing agent such as Jones reagent, for example, to give the correpsonding propionic acid 7. Alternatively, the pyrazoline 6 may be dehydrated with p-toluenesulfonic acid or trifluoroacetic acid, for example, in a suitable solvent such as benzene or toluene to the corresponding pyrazole alcohol 8 which is then oxidized to the acid 7 with a suitable oxidizing agent such as chromic acid. In those cases in which the 5-hydroxy-2-pyrazoline is too unstable to isolate, the pyrazole alcohol is obtained. The hydroxamic acid 9 is synthesized from the propionic acid 7 by reacting it first with an acid chloride such as oxalyl chloride in a suitable solvent such as tetrahydrofuran to form the corresponding acyl chloride which is then reacted with an N-lower alkylhydroxylamine in an inert solvent. The reaction is preferably carried out at temperatures between 0° C. and room temperature. The esters of the hydroxamic acids are prepared by reaction with an acid chloride such as acetyl chloride in a suitable solvent such as chloroform. The reaction is preferably carried out at temperatures between −10° C. and room temperature.

5. 3-[1-(2-benzothiazolyl)-5-(4-chlorophenyl)-3-pyrazolyl]propionic acid (16)

6. 3-[5-(4-chlorophenyl)-1-(6-methoxy-2-benzothiazolyl)-3-pyrazolyl]-N-hydroxy-N-methyl]propanamide (22)

7. N-acetoxy-3-[5-(4-chlorophenyl)-1 (4-chloro-2-benzothiazolyl)-3-pyrazolyl]-N-methylpropanamide (25)

8. 3-[1-(4-methoxyphenyl)-5-[2-(N-methyl)pyrollyl]-3-pyrazolyl]-propionic acid (30)

9. 3-[1-(4-methoxyphenyl)-5-(3-pyridyl)-3-pyrazolyl]propionic acid hydrochloride (31)

10. 3-[1-(4-methoxyphenyl)-5-(2-thienyl)-3-pyrazolyl]-N-hydroxy-N-methylpropanamide (32)

SCHEME 2

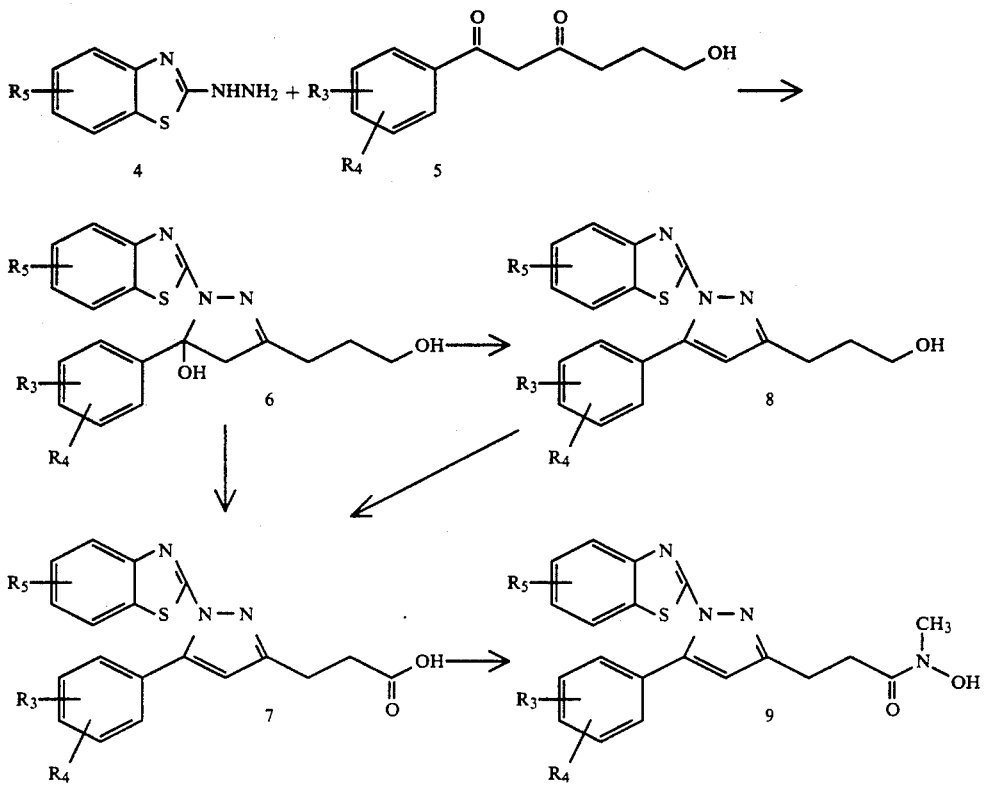

Some of the intermediate compounds are novel compounds and as such are a part of this invention. The starting materials for the novel compounds are prepared by general techniques known to those skilled in the art.

Specific, particularly preferred N-1 and C-5 heterocyclic pyrazole compounds are named hereinbelow, followed by a parenthesized numeral for ease of identification and correlation with the syntheses and antiinflammation study described in detail hereinafter.

The preferred species of this invention include:
1. 1-(4-methoxy-2-benzothiazolyl)-5-(4-chlorophenyl)-5-hydroxy-3-(3-hydroxy-propyl)-2-pyrazoline (6)
2. 5-(4-chlorophenyl)-3-(3-hydroxypropyl)-1-(4-methyl-2-benzothiazolyl)pyrazole (10)
3. 5-(4-chlorophenyl)-3-(3-hydroxypropyl)-1-(4-methoxy-2-benzothiazolyl)pyrazole (12)
4. 3-[1-(4-chloro-2-benzothiazolyl)-5-(4-chlorophenyl)-3-pyrazolyl]propionic acid (15)

A pharmaceutical composition that comprises an anti-inflammatory amount of a N-1 and C-5 heterocyclic pyrazole compound of this invention dispersed in a pharmaceutically acceptable carrier is also contemplated herein. The composition comprises a unit dosage of the substituted pyrazole compound.

The substituted pyrazole compounds of this invention are capable of inhibiting the lipoxygenase enzyme pathway and/or the cyclooxygenase (prostaglandin synthetase) enzyme pathway. In preferred practice, the substituted pyrazole compound of the pharmaceutical composition is capable of inhibiting both the lipoxygenase and the cyclooxygenase enzyme pathways in the amount at which that substituted pyrazole compound is present in the pharmaceutical composition, when that composition is introduced as a unit dose into an appropriate mammal such as a laboratory rat.

The term "unit dosage" and its grammatical equivalent is used herein to refer to physically discrete units suitable as unitary dosages for human patients and other warm blooded animals, each unit containing a predetermined effective, pharmacologic amount of the active ingredient calculated to produce the desired pharmacological effect in association with the required physiologically tolerable carrier, e.g., a diluent or a vehicle. The specifications for the novel unit dosage forms of this invention are dictated by and are directly dependent on (a) the unique characteristics of the active ingredient, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions and suspensions.

The active ingredient is referred to herein as being dispersed in the carrier. Thus, the dispersion formed can be a simple admixture, a non-settling dispersion as in the case of certain emulsions, or as an ultimate dispersion, a true solution.

The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligrams per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans.

As is seen from the data discussed hereinafter, orally administered unit doses containing about 1 to about 50 milligrams of N-1 and C-5 heterocyclic pyrazole per kilogram of laboratory rat body weight (e.g., about 200 grams each) were useful in reducing inflammation. These results are contrary to those reported by Virmani et al., Indian J. Chem., Sect. B, 17:472–477 (1979) who reported compounds that are structurally similar to those described herein were not active as anti-inflammatory agents.

Physiologically tolerable carriers are well known in the art. Exemplary of liquid carriers are aqueous solutions that contain no materials in addition to the substituted pyrazole compound, or contain a buffer such as sodium phosphate at physiological pH value, saline and the like.

Liquid compositions can also contain liquid phases in addition to and to the exclusion of water. Exemplary of such additional liquid phases are glycerin and vegetable oils such as cottonseed oil.

Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such a cane or beet sugar, sodium saccharin, sodium cyclamate and the dipeptide methyl ester sweeteneer sold under the trademark NUTRASWEET (aspartame) by G. D. Searle Co.

A method for alleviating inflammation in a mammal exhibiting an inflammatory condition is also contemplated. The method comprises administering to that mammal an effective amount of a pharmaceutical composition that includes a unit dose of an active ingredient that is the before-described substituted pyrazole compound dispersed in a pharmaceutically acceptable carrier. The pharmaceutical composition is preferably maintained within the mammal until the substituted pyrazole compound is cleared from the mammal's body by natural means such as excretion or metabolism.

The pharmaceutical composition can be administered orally, topically or by injection, by means well known in the art. In preferred practice, the composition is admininstered orally as a tablet, capsule or aqueous dispersion.

IN VIVO ALLEVIATION OF INFLAMMATION

Polyarthritis was induced in Lewis strain laboratory rats (weight=about 200 grams) by injection of a suspension of Mycobacterium butyricum in mineral oil into the subplantar tissue of the mammal's hind paws. On day 10 after the injection, the rats were assigned to groups, and paw volumes and body weights were recorded. Paw volumes of the contralateral, uninjected hind paw were determined by mercury plethylsmography. Per os (p.o.) dosing began and continued for five consecutive days thereafter. On day 14 after the initial injection, approximately four hours after the final dose was administered, paw volumes and body weights were recorded and quantitated.

Anti-inflammatory activity of the substituted pyrazole compounds is expressed a the percent inhibition of paw volume increase.

The compounds of this invention were tested for their antiinflammatory activity. The results of this study for representative compounds of the invention of the following structure are show below.

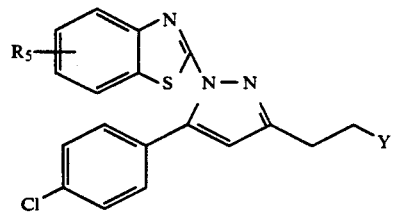

| No. | $R_5$ | Y | % INH. p.o. (mpk) |
|---|---|---|---|
| 6 | 6-methoxy | $CH_2OH$ | 28% @ 40 |
| 10 | 4-methyl | $CH_2OH$ | 49% @ 30 |
| 12 | 4-methoxy | $CH_2OH$ | 21% @ 15 |
| 15 | 4-chloro | $CO_2H$ | 26% @ 15 |
| 16 | hydrogen | $CO_2H$ | 60% @ 15 |
| 22 | 6-methoxy | $CON(OH)CH_3$ | 13% @ 15 |
| 25 | 4-chloro | $CON(OCOCH_3)CH_3$ | 31% @ 15 |

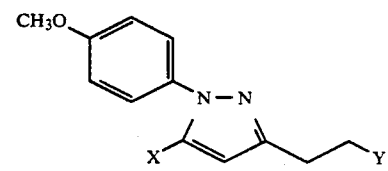

| No. | X | Y | % INH. p.o. (mpk) |
|---|---|---|---|
| 30 | N-Methylpyroll-2-yl | $CO_2H$ | 30% @ 40 |
| 31 | Pyrid-3-yl | $CO_2H$ | 9% @ 10 |

-continued

| 32 | Thien-2-yl | CON(OH)CH$_3$ | 31% @ 15 |

BEST MODES FOR CARRYING OUT THE INVENTION

Melting points (mp) were determined on a Thomas-Hoover apparatus, and are uncorrected. Nuclear magnetic resonance (NMR) spectra or hydrogen atoms were measured in the indicated solvent with tetramethylsilane (TMS) as the internal standard on a Varian T-60A or an IBM WP-100 spectrometer. The values are expressed in parts per million downfield from TMS. Parenthesized, underlined hydrogens were assigned to the resonance positions immediately before the parentheses. EI and CI mass spectra were obtained on a Finnigan 1015D quadrupole mass spectrometer coupled to a Finnigan 9500 gas chromatograph or a Finnigan MAT 8230 Double Focusing high resolution mass spectrometer. In tables 1-4 the elemental analysis for each compound was within ±0.4%.

EXAMPLE 1

1-(2-Benzothiazolyl)-5-(4-chlorophenyl)-5-hydroxy-3-(3- hydroxypropyl)-2-pyrazoline (1)

6-(4-Chlorophenyl)-4,6-diketohexanol (7.2 g, 30 mM) was treated with 2-hydrazinobenzothiazole (4.96 g, 30 mM) in pyridine (5 ml) and MeOH (150 ml) at reflux for 2 hr and then allowed to stand at RT for 48 hr. The solvents were removed in vacuo and the crude residue purified by flash chromatography on silica with Et$_2$O:Et$_3$N (2.5%) as eluent. The title compound (1) was obtained as a pale yellow solid, (3.15 g, mp=132°-134° C.) upon recrystallization from Et$_2$O:hexane. NMR(CDCl$_3$) δ 3.2 (2H, C$_4$-H); MS, m/e 387 (M+).

Anal. Calcd. for C$_{19}$H$_{18}$ClN$_3$O$_2$S: C, 58.83; H, 4.68; N, 10.83. Found: C, 58.84; H, 5.04; N, 10.83.

Following the above procedure, but employing the appropriately substituted hydrazino benzothiazole afforded the compounds of Table 1.

TABLE 1

| # | R | Melting Point | MS m/e (M+) | C, H, N |
|---|------|-------------|-------------|---------|
| 2 | 4-OMe | 171-173° C. | 417 | x x x* |
| 3 | 4-Me | 133-135° C. | 401 | x x x |
| 4 | 4-Cl | 128-129° C. | 421 | x x x |

*½ hydrate

Following a similar procedure, but employing 2-hydrazinothiazole afforded 5-(4-Chlorophenyl)5-hydroxy-3-(3-hydroxypropyl)-1-(2-thiazolyl)-2-pyrazoline (5) as a white solid, mp=146°-147° C.; MS, m/e 337 (M+).

EXAMPLE 2

5-(4-Chlorophenyl)-3-(3-hydroxypropyl)-1-(6-methoxy-2-benzothiazolyl)pyrazole (6)

6-(4-Chlorophenyl)-4,6-diketohexanol (14.43 g, 60 mM) was treated with 2-hydrazino-6-methoxybenzothiazole (11.72 g, 60 mM) in pyridine (10 ml) and MeOH (300 ml) at reflux for 72 hr. Work-up as described in Example 1 followed by recrystallization from MeOH afforded the title compound 6 as a white solid (19.4 g), mp=123°-125° C.; NMR(CDCl$_3$) δ 6.3 (s, 1H, C$_4$-H); MS, m/e 399 (M+).

Anal. Calcd. for C$_{20}$H$_{18}$ClN$_3$O$_2$S: C. 60.07; H, 4.54; N, 10.51. Found: C, 60.46; H, 4.36; N, 10.43.

Following the procedure of Example 2, but employing 2-hydrazinothiazoline afforded 5-(4-chlorophenyl)-3-(3-hydroxypropyl)-1-(2-thiazolinyl)pyrazole (7) as a yellow oil: MS, m/e 321 (M+)

Anal. Calcd. for C$_{15}$H$_{16}$ClN$_3$OS: C, 55.98; H, 5.01; N, 13.06. Found: C, 56.13; H, 5.33; N, 12.72.

Likewise, employing 3-chloro-6-hydrazinopyridazine afforded 5-(4-chlorophenyl)-1-(3-chloropyridazin-6-yl)-3-(3-hydroxypropyl)pyrazole (8) as a white solid, mp=131°-133° C.; MS, m/e 348 (M+).

Anal. Calcd. for C$_{16}$H$_{14}$Cl$_2$N$_4$O: C, 55.03; H, 4.04; N, 16.04. Found: C, 54.76; H, 4.13; N, 15.81.

Likewise, employing 3,5-dichloro-4-hydrazino pyridine afforded 5-(4-chlorophenyl)-1-(3,5-dichloropyridin-4-yl)-3-(3-hydroxypropyl)pyrazole (9) as a white solid, mp=108°-110° C., MS, m/e 381 (M+).

Anal. Calcd. for C$_{17}$H$_{14}$Cl$_3$N$_3$O: C, 53.35; H, 3.69; N, 10.98 Found: C, 53.35; H, 3.69, N, 10.92

EXAMPLE 3

5-(4-Chlorophenyl)-3-(3-hydroxypropyl)-1-(4-methyl-2-benzothiazolyl)pyrazole (10)

Compound 3 (1.2 g, 3.0 mM) in benzene (250 ml) was treated with p-toluenesulfonic acid (50 mg) and heated at reflux for 18 hr. The solvent was removed in vacuo, the residue dissolved in EtOAc, washed (brine), dried (Na$_2$SO$_4$) and evaporated to give a semi-solid which was recrystallized from Et$_2$O:hexane to afford the title compound as an off-white solid, mp=112°-114° C., NMR(CDCl$_3$) δ 6.28 (s, 1H, C$_4$-H); MS, m/e 383 (M+).

Anal. Calcd. for C$_{20}$H$_{18}$ClN$_3$OS: C, 62.57; H, 4.73; N, 10.95. Found: C, 62.75; H, 4.59; N, 11.00.

Following the above procedure, but employing the remaining 5-hydroxy-2-pyrazolines described in Table 1 gave the compounds of Table 2.

TABLE 2

| # | R | Melting Point | MS m/e (M+) | C, H, N |
|----|------|-------------|-------------|---------|
| 11 | H | 136-138° C. | 369 | x x x |
| 12 | 4-OMe | 139-140° C. | 399 | x x x |
| 13 | 4-Cl | 153-155° C. | 403 | x x x |

*½ hydrate

Likewise, employing compound 5 afforded 5-(4-chlorophenyl)-3-(3-hydroxypropyl)-1-(2-thiazolyl)-pyrazole (14) as a white solid following recrystallization from Et$_2$O:hexane, mp=76°-78° C., MS, m/e 19 (M+).

Anal. Calcd. for C$_{15}$H$_{14}$ClN$_3$OS: C, 56.33; H, 4.41; N, 13.14. Found: C, 56.29; H, 4.47; N, 12.96.

EXAMPLE 4

3-[1-(4-Chloro-2-benzothiazolyl)-5-(4-chlorophenyl)-3-pyrazolyl]propionic acid (15)

Compound 13 (8.4 g, 20.8 mM) in acetone (1.5 l) was treated with 2N H$_2$Cr$_2$O$_7$ (25 ml) and allowed to stir at RT for 4 hr. The chromium salts were filtered, and the filtrate evacuated in vacuo to give a crude residue which was dissolved in EtOAc, washed (brine), dried (Na$_2$SO$_4$) and evaporated to give a solid which was recrystallized from EtOAc:hexane to afford the title compound 15 as a white solid, mp=232°-234° C.; MS, m/e 417 (M$^{30}$).

Anal. Calcd. for C$_{19}$H$_{13}$Cl$_2$N$_3$O$_2$S.1/4H$_2$O: C, 53.97; H, 3.22, N, 9.94. Found: C, 53.70; H, 3.05; N, 9.89.

Following the above procedure, but substituting the appropriate 3-hydroxypropyl pyrazole for compound 13 afforded the compounds of Table 3.

TABLE 3

| # | R | Melting Point | MS m/e (M+) | C, H, N |
|---|---|---|---|---|
| 16 | H | 201-203° C. | 383 | x x x |
| 17 | 6-OMe | 176-178° C. | 413 | x x x |
| 18 | 4-OMe | 192-194° C. | 413 | x x x |
| 19* | 4-Me | 180-182° C. | 397 | x x x |

*Compound 19 was synthesized directly from 5-hydroxy-2-pyrazoline 3 using the conditions described in Example 4.

Likewise, employing the 3-hydroxypropyl pyrazole 8 of Example 2 afforded 3-(5-(4-chlorophenyl)-1-(3-chloropyridazin-6-yl)-3-pyrazolyl]propionic acid (20) as a white solid, mp=203°-204° C.; MS, m/e 362 (M+).

Anal. Calcd. for C$_{16}$H$_{12}$Cl$_2$N$_4$O$_2$: C, 52.91; H, 3.33; N, 15.43. Found: C, 52.96; H, 3.47; N, 15.37.

EXAMPLE 5

3-[5-(4-Chlorophenyl)-1-(4-methyl-2-benzothiazolyl)-3-pyrazolyl]-N-hydroxy-N-methylpropanamide (21)

Compound 19 (3.14 g, 7.9 mM) in THF (150 ml) and DMF (0.3 ml) was cooled to 0° C. and treated with oxalyl chloride (0.84 ml), warmed to RT and stirred 3 hr. The solvent was removed in vacuo and the resulting dark brown residue was dissolved in THF (75 ml) and added over 1 hr to a cold solution of N-methylhydroxylamine hydrochloride (1 g) in THF (55 ml), H$_2$O (28 ml) and Et$_3$N (4.6 ml) and then stirred at RT for 3 hr. The solvent was evaporated in vacuo and the residue purified by chromatography on silica and recrystallized from EtOAc:Et$_2$O to afford the title compound 21 as a white solid, mp=156°-158° C., MS, m/e 426 (M+).

Anal. Calcd. for C$_{21}$H$_{19}$ClN$_4$O$_2$S.1/4H$_2$O: C, 58.46; H, 4.56, N, 12.99. Found: C, 58.46; H, 4.33; N, 13.00.

Following the above procedure, but employing the pyrazole propionic acids described in Example 4, afforded the compounds of Table 4.

TABLE 4

| # | R | Melting Point | MS m/e (M+) | C, H, N |
|---|---|---|---|---|
| 22 | 6-OMe | 127-129° C. | 442 | x x x |
| 23 | 4-OMe | 144-145° C. | 442 | x x x |
| 24 | 4-Cl | 177-179° C. | 446 | x x x |

A mixture of compound 24 (750 mg, 1.68 mM), NaHCO$_3$ (141 mg, 1.68 mM) and molecular sieves (4 Å, 250 mg) in CHCl$_3$ (6 ml) was cooled to −10° C. under a N$_2$ atmosphere and treated dropwise with acetyl chloride (0.36 ml, 5.06 mM) in CHCl$_3$ (2.5 ml) and the resulting mixture stirred for 2 hr and then at RT for 22 hr. The reaction mixture was filtered and the filtrate evaporated in vacuo and the - resulting solid recrystallized from Et$_2$O to afford N-Acetoxy-3-[5-(4-chlorophenyl)-1-(4-chloro-2-benzothiazolyl)-3-pyrazolyl]-N-methyl-propanamide (25) as a white solid, mp=159°-160° C., MS, m/e 488 (M+).

Anal. Calcd. for :C$_{22}$H$_{18}$Cl$_2$N$_4$O$_3$S: C, 53.99; H, 3.71; N, 11.45 Found: C, 54.30; H, 3.75; N, 11.34

EXAMPLE 6

Synthesis of 6-Heterocyclic-4,6-diketohexanoic acids

Compounds 26, 27 and 28 were synthesized by the following general procedure. To a reaction vessel containing anhydrous THF (250 ml) and diisopropylamine (14 ml, 0.1 Mole) stirring under nitrogen at 0° C. was added by syringe, n-BuLi (1.6M, 62.5 ml, 0.1 Mole). The vessel was then cooled to −78° C. Alternatively, lithium hexamethyldisilazide (0.1 Mole) may be employed as the base in place of lithium diisopropylamide.

The appropriately substituted acetyl heterocycle (0.1 Mole) in anhydrous THF (50 ml) was added and the resulting solution allowed to stir for 30 minutes at −78° C. and succinic anhydride (4.0 g, 0.04 mole) in THF (100 ml) was added via syringe. The solution was allowed to stir for 1 hr at −78° C., warmed to RT for 1 hr and poured into 5% HCl (250 ml). The mixture was extracted with Et$_2$O (2×300 ml) and the combined ether extract was extracted with 10% NaOH (100 ml). The NaOH layer was separated and acidified with 4N HCl, and reextracted with Et$_2$O (2×300 ml). The combined ether layers were dried (Na$_2$SO$_4$), filtered and concentrated in vacuo. The resultant residues were recrystallized from the appropriate solvent to afford the following compounds:

6-[2-(N-methyl)pyrrolyl]-4,6-dioxohexanoic acid (26), tan solid, mp=95°-97° C.; MS, m/e 223 (M+).

Anal Calcd. for C$_{11}$H$_{13}$NO$_4$: C, 59.18; H, 5.87; N, 6.27. Found: C, 59.03; H, 6.12; N, 6.07.

4,6-Dioxo-6-(3-thienyl)hexanoic acid (27), yellow solid, mp=150°-153° C.; MS, m/e 226 (M+).

Anal. Calcd. for C$_{10}$H$_{10}$O$_4$S: C, 53.08; H, 4.48. Found: C, 53.30; H, 4.52.

4,6-Dioxo-6-(2-thienyl)hexanoic acid (28), yellow solid, mp=100°-101° C.; MS, m/e 226 (M+).

Anal. Calcd. for $C_{10}H_{10}O_4S$: C, 53.08; H, 4.48. Found C, 52.85; H, 4.34.

EXAMPLE 7

4,6-Dioxo-6-(3-pyridyl)hexanoic acid (29)

The procedure described in Example 6 was followed employing 3-acetylpyridine as the acetylheterocycle with the following changes. The lithio salt of 3-acetylpyridine formed a gel-like precipitate which was sonicated before and after the addition of succinic anhydride. When the reaction was complete, $H_2O$ (150 ml) and $Et_2O$ (50 ml) were added, the aqueous layer separated, acidified with 10% HCl to pH 1 and washed with $Et_2O$ (50 ml). The pH of the aqueous layer was then adjusted to pH 6.5 with 1N NaOH at which point a white solid precipitated and was filtered, washed with MeOH and dried to afford the title compound 29 (61%) as a tan solid, mp=156°-158° C. (Recry. acetone), MS, m/e 221 (M+).

Anal. Calcd. for $C_{11}H_{11}NO_4$: C, 59.72; H, 5.01; N, 6.33. Found: C, 59.65; H, 5.03; N, 6.41.

EXAMPLE 8

3-[1-(4-Methoxyphenyl)-5-[2-(N-methyl)pyrollyl]-3-pyrazolyl]-propionic acid (30)

Compound 30 and the related heterocyclic propionic acids were synthesized by the general procedure below.

A mixture of the appropriate 6-heterocyclic-4,6-diketo-hexanoic acid, (0.1 Mole) synthesized as described in Example 6, in methanol (750 ml) containing $Et_3N$ (0.2 Mole) was treated with 4-methoxyphenylhydrazine hydrochloride (17.4 g, 0.1 Mole) at RT for 1 hr. If the reaction was incomplete at this point, it was refluxed until complete. The resulting darkened solution was evaporated in vacuo and taken up in $Et_2O$ (700 ml); the ether solution was washed with aqueous 1N HCl (350 ml), brine, dried ($Na_2SO_4$), decolorized, evaporated in vacuo and chromatographed on Silica and when appropriate recrystallized from $Et_2O$ to give the pyrazole propionic acids which were used without further purification in Example 10.

Compound 30 was isolated as a yellow oil, MS, m/e 325 (M+).

Anal. Calcd. for $C_{18}H_{19}N_3O_3.\frac{1}{4}H_2O$: C, 65.53; H, 5.96; N, 12.73 Found: C, 65.75; H, 6.06; N, 12.58.

EXAMPLE 9

3-[1-(4-Methoxyphenyl)-5-(3-pyridyl)-3-pyrazolyl]-propionic acid hydrochloride (31)

Compound 29 (2.21 g, 10 mM) in methanol (150 ml) containing $Et_3N$ (2 ml) was treated with 4-methoxyphenylhydrazine hydrochloride (1.85 g, 10.6 mM) at RT for 4 hr. The solvent was removed in vacuo and the residue was partitioned between 5% NaOH and $Et_2O$. The basic aqueous layer was separated and acidified with 10% HCl to pH 2. Saturated brine was added and the aqueous layer was exhaustively extracted with $CH_2Cl_2$. The combined $CH_2Cl_2$ layers were concentrated to give the title compound 31 as a tan crystalline solid (Recry. Acetone, 1.87 g, 52%) mp=226°-228° C., MS, m/e 323 (M+).

Anal. Calcd. for $C_{18}H_{17}N_3O_3.HCl$: C, 60.08; H, 5.04; N, 11.68. Found: C, 60.17; H, 5.01; N, 11.71.

EXAMPLE 10

3-[1-(4-methoxyphenyl)-5-(2-thienyl)-3pyrazolyl]-N-hydroxy-N-methylpropanamide (32)

Employing the pyrazole propionic acids synthesized by the procedures of Examples 6 and 8 and following the general procedure described below afforded compounds 32, 33 and 34.

To a solution of the appropriate pyrazole propionic acid (2.77 mM) in tetrahydrofuran (20 ml) at 0° C., was added one drop of dimethyl formamide and oxalyl chloride (0.29 ml, 33 mM). After 0.5 hr the cooling bath was removed and stirring was continued for an additional 0.5 hr. The reaction mixture was concentrated in vacuo to remove any excess oxalyl chloride, and the acid chloride was taken up into THF (10 ml).

To a solution of methylhydroxylamine hydrochloride (0.35 g, 4.16 mM) and triethylamine ($Et_3N$) (1.55 ml, 11.10 mM) in THF, $H_2O$ (10 ml:5 ml) at 0° C., was added the THF solution of the acid chloride dropwise over a 45 minute period. The cooling bath was removed, and the reaction mixture was stirred for 1 hr, diluted to 100 ml with EtOAc, washed with $H_2O$, dried ($MgSO_4$), filtered, and concentrated in vacuo. Chromatography (silica gel) of the residue with EtOAc as eluent, followed by recrystallization from $CH_2Cl_2$: hexane gave the following compounds.

Compound 32, tan foam; MS, m/e 357 (M+).

Anal. Calcd. for $C_{18}H_{19}N_3O_3S$: C, 60.48; H, 5.36; N, 11.76. Found: C, 60.60; H, 5.70; N, 11.63.

3-[1-(4-Methoxyphenyl)-5-(3-thienyl)-3-pyrazolyl]-N-hydroxy-N-methylpropanamide (33), tan solid, mp=149°-151° C. (Recry. $Et_2O$), MS, m/e 357 (M+).

Anal. Calcd. for $C_{18}H_{19}N_3O_3S$: C, 60.48; H, 5.36; N, 11.76 Found: C, 60.31; H, 5.41; N, 11.42

3-[5-(2-Furyl)-1-(4-methoxyphenyl)-3-pyrazolyl]-N-hydroxy-N-methylpropanamide (34), yellow oil, MS, m/e 341 (M+).

Anal. Calcd. for $C_{18}H_{19}N_3O_4.\frac{1}{2}H_2O$: C, 61.70; H, 5.75; N, 11.99 Found: C, 61.99; H, 5.90; N, 11.58

EXAMPLE 11

N-Hydroxy-3-[1-(4-methoxyphenyl)-5-(3-pyridyl)-3-pyrazolyl]-N-methylpropanamide Monoformate (35)

To a solution of compound 31 (0.9 g, 2 5 mM) in $CH_2Cl_2$ (25 ml) at RT was added DMF (0.2 ml) and oxalyl chloride (1.26 g, 10 mM). After stirring for 0.5 hr, the reaction mixture was evaporated in vacuo, redissolved in $CH_2Cl_2$ (25 ml) and added dropwise to a solution of methylhydroxylamine hydrochloride (0.84 g, 10 mM) and $Et_3N$ (3.7 ml) in $CH_2Cl_2$ (50 ml) at 0° C. The reaction was stirred for 10 min and poured into a 1:1 stirred mixture of $Ch_2Cl_2:H_2O$. The $CH_2Cl_2$ layer was separated, washed ($H_2O$ and then brine), dried ($Na_2SO_4$) and evaporated in vacuo to give a semi-solid which was purified by column chromatography on Silica employing Hexane:40EtOAc:1% MeOH:0.1% $HCO_2H$ as eluent. The title compound 35 was obtained as a tan foam as the monoformate salt; MS, m/e 352 (M+).

Anal Calcd. for $C_{19}H_{20}N_4O_3.HCO_2H$: C, 60.29; H, 5.56; N, 14.06 Found: C, 59.96; H, 5.55; N, 14.08

EXAMPLE 12

3-[1-(4-Methyl-2-benzothiazolyl)-5-(3-thienyl)-3-pyrazolyl]priopionic acid (36)

Following the procedure described in Example 8 employing 6-(3-thienyl)-4,6-diketohexanoic acid as the diketo acid and substituting 2-hydrazino-4-methylbenzothiazole for 4-methoxy-phenylhydrazine followed by treatment with trifluoroacetic acid affords the title compound 36; m.p.=173°-174° C.

Anal. Calcd. for $C_{18}H_{15}N_3O_2S_2 \cdot \frac{1}{2}H_2O$: C, 57.81; H, 4.18; N, 11.24 Found: C, 57.60; H, 3.85; N, 11.22

EXAMPLE 13

3-[1-(4-Methyl-2-benzothiazolyl)-5-(3-thienyl)-3-pyrazolyl]-N-hydroxy-N-methylpropanamide (37)

Following the procedure described in Example 5, but substituting Compound 36 for Compound 19 affords the title compound 37; m.p.=142°-143° C.

What is claimed is:

1. A compound of the formula

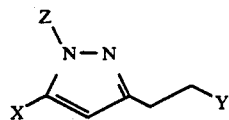

wherein Z is selected from the group consisting of phenyl, substituted phenyl wherein the substituents are $R_1$ and $R_2$, and $R_1$ and $R_2$ are selected from hydrogen, lower, alkyl, lower alkoxy, amino, acetamido, halo, phenyl, hydroxyl, lower alkylsulfonyl, lower alkylthio, nitro, trifluoromethyl, ωtrifluoromethyl lower alkoxy, or where $R_1,R_2$ are taken together with the phenyl group they form a naphthyl or substituted naphthyl group; X is selected from the group consisting of 2-thienyl, 3-thienyl, 3-thienyl, 2-furanyl, and 2-N-lower alkylpyrollyl; Y is CON(OH) lower alkyl or CON(OCOR$^5$) lower alkyl wherein $R_5$ is lower alkyl or a pharmaceutically acceptable salt thereof.

2. The compound of claim 1, which compound is 3-[1-(4-methoxyphenyl)-5-(2-thienyl)-3-pyrazolyl]-N-hydroxy-N-methylpropanamide.

3. A pharmaceutical composition for topical, oral, parenteral and aerosol administration, comprising an effective amount of substituted pyrazole compound according to claim 1 as active ingredient dispersed in a pharmaceutically acceptable carrier.

4. The pharmaceutical composition according to claim 3 wherein said substituted pyrazole compound is capable of inhibiting both the cyclooxygenase and lipoxygenase pathways in the amount present in the composition when said composition is introduced into a mammal.

5. A method of alleviating inflammation in a mammal exhibiting an inflammatory response comprising administering to said mammal the pharmaceutical composition according to claim 3.

6. A method for treating inflammatory conditions of skin, including psoriasis or other dermatitis, comprising administering to said mammal a pharmaceutical composition according to claim 3.

* * * * *